United States Patent
Bailey et al.

(10) Patent No.: US 11,562,875 B2
(45) Date of Patent: Jan. 24, 2023

(54) HYBRID AIR AND LIQUID X-RAY COOLING SYSTEM COMPRISING A HYBRID HEAT-TRANSFER DEVICE INCLUDING A PLURALITY OF FIN ELEMENTS, A LIQUID CHANNEL INCLUDING A COOLING LIQUID, AND A CIRCULATION PUMP

(71) Applicant: Dedicated2Imaging, LLC, Portsmouth, NH (US)

(72) Inventors: Eric M. Bailey, North Hampton, NH (US); Andrew Tybinkowski, Topsfield, MA (US); Charles Landry, Seabrook, NH (US); Jamie Brooks, Amesbury, MA (US); Mark Dieselman, Amesbury, MA (US); Clayton Garland, Barrington, NH (US)

(73) Assignee: Dedicated2Imaging, LLC, Portsmouth, NH (US)

( * ) Notice: Subject to any disclaimer, the term of this patent is extended or adjusted under 35 U.S.C. 154(b) by 107 days.

(21) Appl. No.: 17/045,998

(22) PCT Filed: Mar. 29, 2019

(86) PCT No.: PCT/US2019/024727
§ 371 (c)(1),
(2) Date: Oct. 8, 2020

(87) PCT Pub. No.: WO2019/226232
PCT Pub. Date: Nov. 28, 2019

(65) Prior Publication Data
US 2021/0368609 A1    Nov. 25, 2021

Related U.S. Application Data

(60) Provisional application No. 62/675,397, filed on May 23, 2018.

(51) Int. Cl.
*A61B 6/03*    (2006.01)
*H01J 35/02*   (2006.01)
(Continued)

(52) U.S. Cl.
CPC .............. *H01J 35/13* (2019.05); *A61B 6/032* (2013.01); *A61B 6/035* (2013.01); *A61B 6/40* (2013.01);
(Continued)

(58) Field of Classification Search
CPC . A61B 6/032; A61B 6/035; A61B 6/40; H01J 35/02; H01J 35/06; H01J 35/08;
(Continued)

(56) References Cited

U.S. PATENT DOCUMENTS

| | | | |
|---|---|---|---|
| 4,165,472 A | * | 8/1979 | Wittry .................. H01J 35/106 313/30 |
| 4,210,813 A | | 7/1980 | Romanovsky et al. |

(Continued)

FOREIGN PATENT DOCUMENTS

| | | |
|---|---|---|
| CN | 2643474 Y | 9/2004 |
| DE | 498823 C | 5/1930 |

(Continued)

*Primary Examiner* — Allen C. Ho

(57) ABSTRACT

A cooling system used in an X-ray generator having a cathode and anode that includes a target having a focal spot, wherein heat is generated in the anode and focal spot during operation of the X-ray generator. The system includes a heat transfer element attached to the anode wherein the heat transfer element includes a plurality of fin elements that transfer heat from the anode to surrounding air to cool the anode. The system also includes a liquid channel formed in the anode, wherein the liquid channel includes a cooling liquid. The liquid channel is located adjacent the target wherein heat from the focal spot is transferred to the cooling liquid to cool the focal spot wherein the heat transfer
(Continued)

element, liquid channel and anode are unistructurally formed. Further, the cooling system includes a circulation pump that moves the cooling liquid in the liquid channel.

18 Claims, 2 Drawing Sheets

(51) Int. Cl.
| | |
|---|---|
| *H01J 35/06* | (2006.01) |
| *H01J 35/08* | (2006.01) |
| *H01J 35/12* | (2006.01) |
| *H01J 35/16* | (2006.01) |
| *H05G 1/02* | (2006.01) |
| *A61B 6/00* | (2006.01) |

(52) U.S. Cl.
CPC .............. *H01J 35/06* (2013.01); *H01J 35/08* (2013.01); *H01J 35/112* (2019.05); *H01J 35/12* (2013.01); *H01J 35/16* (2013.01); *H05G 1/025* (2013.01); *H01J 2235/1204* (2013.01); *H01J 2235/1262* (2013.01); *H01J 2235/1283* (2013.01)

(58) Field of Classification Search
CPC .......... H01J 35/112; H01J 35/12; H01J 35/13; H01J 35/16; H01J 2235/1204; H01J 2235/1262; H01J 2235/1283; H05G 1/02; H05G 1/025
USPC ................ 378/127, 130, 141, 199, 200, 143
See application file for complete search history.

(56) References Cited

U.S. PATENT DOCUMENTS

| | | | | |
|---|---|---|---|---|
| 4,943,989 A | * | 7/1990 | Lounsberry | H01J 35/106 378/127 |
| 5,802,140 A | * | 9/1998 | Virshup | H05G 1/04 378/121 |
| 6,115,454 A | * | 9/2000 | Andrews | H01J 35/105 378/140 |
| 6,215,852 B1 | * | 4/2001 | Rogers | H01J 35/105 378/141 |
| 6,263,046 B1 | * | 7/2001 | Rogers | H01J 35/18 378/140 |
| 6,377,659 B1 | * | 4/2002 | Snyder | H01J 35/107 378/127 |
| 6,519,317 B2 | * | 2/2003 | Richardson | H05G 1/025 378/141 |
| 6,580,780 B1 | * | 6/2003 | Miller | H01J 35/13 378/141 |
| 6,594,341 B1 | * | 7/2003 | Lu | H01J 35/18 378/140 |
| 6,623,160 B2 | * | 9/2003 | McCarthy, Jr. | F25B 1/06 378/130 |
| 6,997,609 B2 | * | 2/2006 | McCarthy, Jr. | H05G 1/025 378/141 |
| 7,056,017 B2 | * | 6/2006 | Daniel | H05G 1/025 378/141 |
| 7,192,189 B2 | * | 3/2007 | Baur | H05G 1/02 378/199 |
| 7,236,571 B1 | * | 6/2007 | Kendall | H01J 35/16 378/141 |
| 7,349,525 B2 | * | 3/2008 | Morton | H01J 35/13 378/124 |
| 7,440,549 B2 | * | 10/2008 | Kerpershoek | H01J 35/106 378/130 |
| 7,543,987 B2 | * | 6/2009 | Canfield | A61B 6/40 378/141 |
| 9,263,225 B2 | * | 2/2016 | Morton | H01J 35/13 |
| 9,648,710 B2 | * | 5/2017 | Smith | H05G 1/025 |
| 10,178,748 B1 | * | 1/2019 | Steck | H01J 35/13 |
| 10,727,023 B2 | * | 7/2020 | Parker | H01J 35/12 |
| 11,266,000 B2 | * | 3/2022 | Chen | H05G 1/04 |
| 2006/0171505 A1 | | 8/2006 | Heidrich et al. | |

FOREIGN PATENT DOCUMENTS

| | | |
|---|---|---|
| JP | S6039747 A | 3/1985 |
| KR | 101089233 B1 | 12/2011 |

* cited by examiner

HYBRID AIR AND LIQUID X-RAY COOLING SYSTEM COMPRISING A HYBRID HEAT-TRANSFER DEVICE INCLUDING A PLURALITY OF FIN ELEMENTS, A LIQUID CHANNEL INCLUDING A COOLING LIQUID, AND A CIRCULATION PUMP

PRIORITY CLAIM

This is a U.S. National Phase application of PCT/US2019/024727 filed on Mar. 29, 2019, which claims the benefit under 35 U.S.C. § 119(e) of U.S. Provisional Application No. 62/675,397 filed on May 23, 2018, both of which are incorporated herein by reference in their entirety and to which this application claims the benefit of priority.

TECHNICAL FIELD

Aspects of the present invention relate to a hybrid system for cooling an X-ray generator and, more particularly, to a hybrid system having a heat transfer element having fins that cool the anode and a liquid channel formed in the anode that cools a focal spot of the X-ray generator wherein the heat transfer element, liquid channel and anode are unistructurally formed.

BACKGROUND

X-rays are typically generated in an X-ray tube having a cathode and a metal anode located in a vacuum chamber. In order to generate X-rays, an electric current is applied to a filament in the cathode that causes the filament to emit electrons. An electric potential applied between the cathode and anode then accelerates the electrons so that the electrons impinge, or collide, on a target surface of the anode to cause the generation of X-rays. The X-rays are then transmitted through an X-ray window of the tube for use in medical imaging, therapeutic radiology and other known uses. The electrons collide on an area of the target surface of the anode known as the focal spot. Less than approximately 1% of the collisions result in the generation of X-rays. More often, the collisions generate substantial amounts of heat in the anode. It is important that the heat generated in the anode is removed so that the X-ray tube is not damaged or otherwise compromised.

In medical X-ray systems, it is frequently desirable to utilize a relatively small focal spot in order to improve resolution of an image, for example. Thus, the removal of heat from the anode becomes more important as the size of the focal spot is reduced. With respect to medical X-ray systems using a stationary anode, a separate cooling system is utilized that pumps cooling liquid through the X-ray tube in order to remove heat from the anode. The cooling liquid is then pumped through a relatively large external liquid-to-air heat exchanger that is used in conjunction with a fan that blows cooling air over the heat exchanger surface to remove heat. This type of cooling system increases the cost, complexity, size and weight (for example, up to 2000 lbs.) of the overall X-ray system. In addition, the use of such cooling systems limits the peak power, peak scan duration, and inter-scan cooling times of the X-ray system.

Other medical X-ray systems utilize a cooling arrangement wherein a heatsink is directly attached to the anode portion of the X-ray tube. Heat from the anode is transferred to the heatsink which is then cooled by blowing cooling air over heatsink. However, this type of cooling arrangement limits the maximum power level available for generating X-rays and results in undesirable recovery times.

SUMMARY OF THE INVENTION

A cooling system is disclosed for an X-ray generator having a cathode and anode that includes a target having a focal spot, wherein heat is generated in the anode and focal spot during operation of the X-ray generator. The system includes a heat transfer element attached to the anode wherein the heat transfer element includes a plurality of fin elements that transfer heat from the anode to surrounding air to cool the anode. The system also includes a liquid channel formed in the anode, wherein the liquid channel includes a cooling liquid. The liquid channel is located adjacent the target wherein heat from the focal spot is transferred to the cooling liquid to cool the focal spot wherein the heat transfer element, liquid channel and anode are unistructurally formed. Further, the cooling system includes a circulation pump that moves the cooling liquid in the liquid channel.

In addition, a method is disclosed of cooling a focal spot and an anode in an X-ray generator wherein the anode includes a target having the focal spot. The method includes cooling the anode by providing a plurality of fin elements on the anode that transfer heat from the anode to surrounding air to cool the anode. The method also includes providing a liquid channel in the anode wherein the liquid channel includes a cooling liquid. The liquid channel is located adjacent to the target to enable the transfer of heat from the focal spot to the cooling liquid to cool the focal spot wherein the fin elements, liquid channel and anode form a unistructure.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which.

To facilitate understanding, identical reference numerals have been used, where possible, to designate identical elements that are common to the figures. The figures are not drawn to scale.

DETAILED DESCRIPTION

Figure 1:
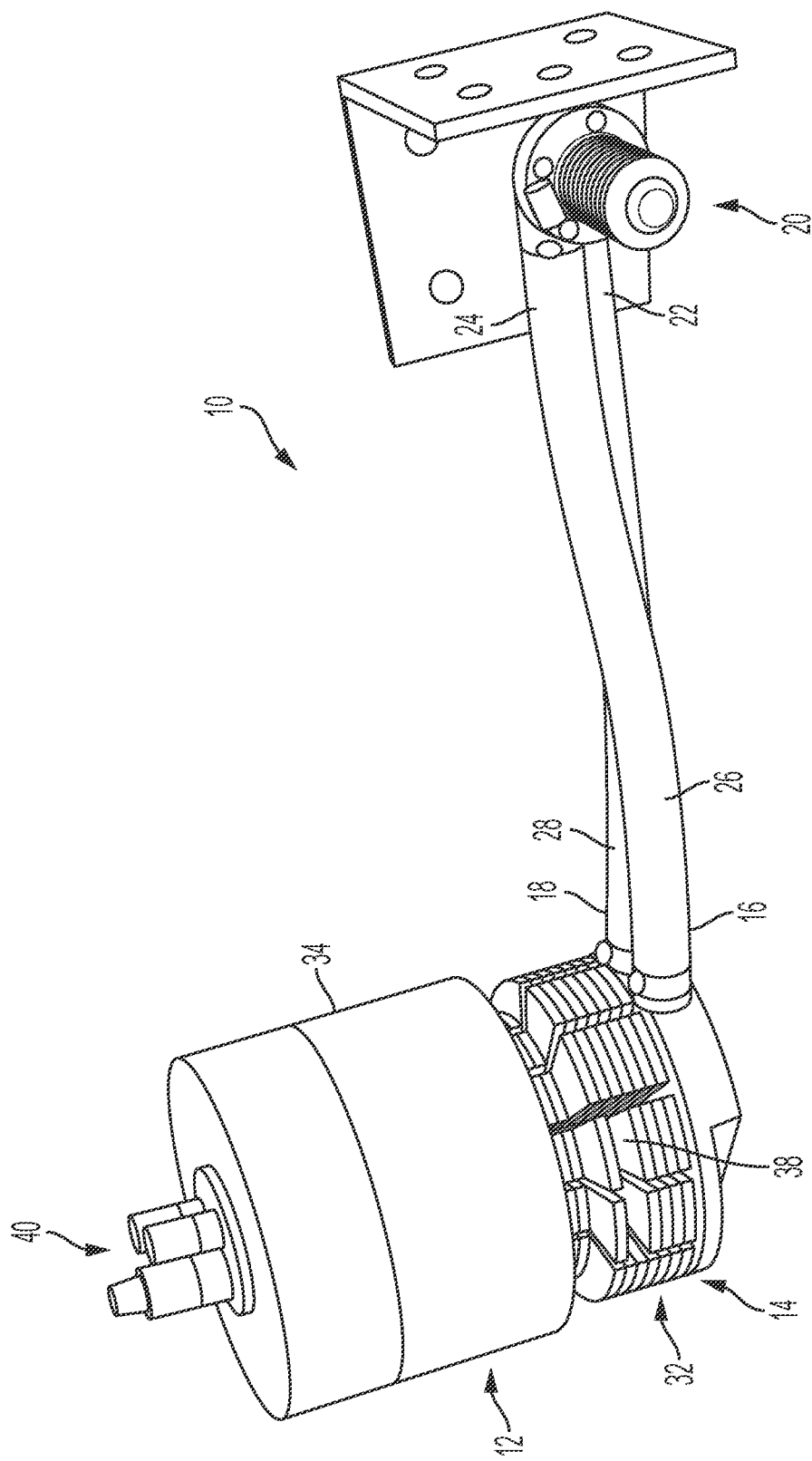
FIG. 1 depicts a perspective view of a hybrid air and liquid cooling system for cooling an X-ray generator in accordance with an aspect of the invention.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Figure 2:
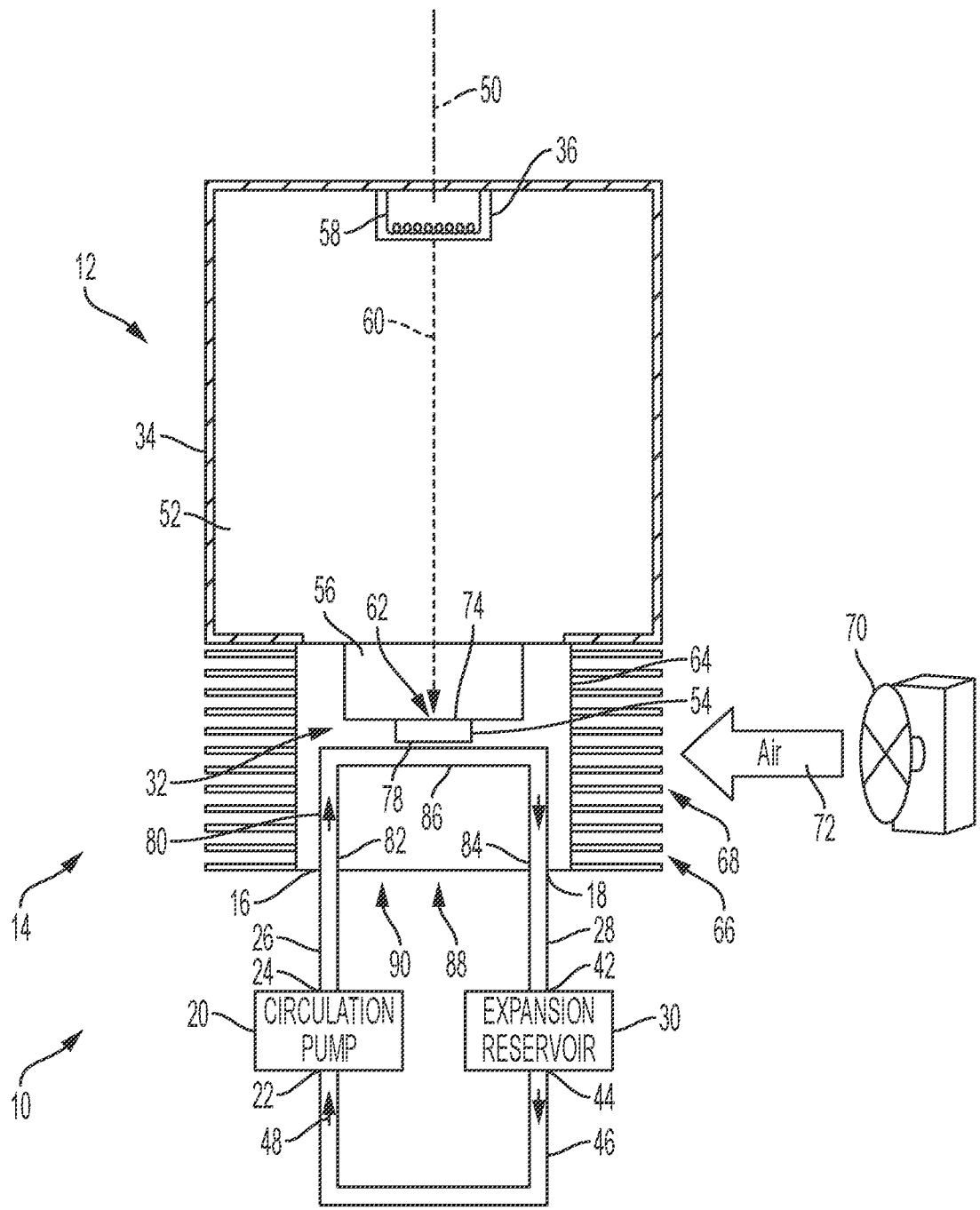
FIG. 2 depicts a schematic cross-sectional view of the cooling system and X-ray generator.

Referring to FIG. 1, a perspective view of a hybrid air and liquid cooling system 10 for cooling an X-ray generator 12 is shown. The cooling system 10 includes a hybrid heat transfer device 14 having a device inlet 16 and device outlet 18 and a circulation pump 20 having a pump intake 22 and pump outlet 24. The pump outlet 24 is connected to the device inlet 16 by a liquid inlet conduit 26. The device outlet 18 is connected to the pump intake 22 by a liquid outlet conduit 28. In an embodiment, an expansion reservoir 30 (FIG. 2) is connected between the device outlet 18 and the pump intake 22 as will be described. The X-ray generator 12 may be an X-ray tube of the type used in an X-ray medical imaging system such as a computed tomography (CT) imaging system, although other types of X-ray tubes may be used. The X-ray generator 12 includes an anode 32 and a housing 34 that houses a cathode 36 (FIG. 2). In an embodiment, the anode 32 is a stationary anode although other types of anodes may be used. In an embodiment, the anode 32 and housing 34 each have a substantially cylindrical shape although other suitable shapes may be used. The device 14 includes an X-ray window 38 fabricated from a material that enables the transmission of X-rays through the device 14 and toward an object to be scanned. The X-ray generator 12 further includes electrical connectors 40 for connection to a high voltage power supply via a monoblock assembly of a CT imaging system.

Referring to FIG. 2, a schematic cross-sectional view of the cooling system 10 and X-ray generator 12 is shown. In an embodiment, the cooling system 10 further includes an expansion reservoir 30 having a reservoir inlet 42 and reservoir outlet 44. The device outlet 18 is connected to the reservoir inlet 42 by the outlet conduit 28 and the reservoir outlet 44 is connected to the pump intake 22 by an intermediate conduit 46. The expansion reservoir 30 serves to accommodate increases in volume of cooling fluid or cooling liquid 48 as will be described. The housing 34 and anode 32 are aligned along a center axis 50 of the X-ray generator 12. The housing 34 includes a vacuum chamber 52 that houses the cathode 36. In an embodiment, the housing 34 includes metal and ceramic sections and is fabricated such that the ceramic section forms a seal with the metal section to maintain a vacuum in the vacuum chamber 52. The ceramic material also serves an electrical insulator. The housing 34 may further include a radiation shield structure that absorbs electrons within the housing 34 that are not being used to generate X-rays so as to avoid further heat generation.

The anode 32 includes a target 54 having a target front 74 and a target rear surface 78 located on an opposite side of the target 54. The target 54 is located in a cutout portion 56 of the anode 32 such that the target front surface 74 is spaced apart from the cathode 36. During use, the vacuum chamber 52 is evacuated to a vacuum level suitable for generating X-rays. An electric current is applied to a filament 58 in the cathode 36 that causes the filament 58 to emit electrons 60. An electric potential applied between the cathode 36 and anode 32 then accelerates the electrons 60 so that the electrons 60 impinge, or collide, on a focal spot 62 of the target front surface 74 to cause the generation of X-rays. In an embodiment, the target front surface 74 is oriented such that the X-rays are directed toward the X-ray window 38 (FIG. 1). The X-rays are then transmitted through the X-ray window 38 and outside of the device 14 for use in medical imaging, therapeutic radiology and other known uses. A substantial amount of the collisions generate heat in the anode 32 and focal spot 62. It is important that the heat generated in the anode 32 and focal spot 62 is removed so that the X-ray generator 12 is not damaged or otherwise compromised.

The anode 32 is defined by an outer surface 64 having a heatsink portion 66. The heatsink portion 66 is fabricated from a thermally conductive material such as copper to facilitate the transfer of heat from the anode 32 to surrounding air. A plurality of thin projections or fins 68 extend from the outer surface 64 of the heatsink portion 66 in a direction substantially transverse to the center axis 50. The fins 68 increase a surface area of the heatsink portion 66 so as to increase the transfer of heat from the anode 32 to surrounding air thus forming a passive heat transfer arrangement. A fan 70 may be used to create an air flow 72 of cooling air over the fins 68 to further increase heat transfer. It is understood that other orientations or configurations for the fins 68 may be used. In addition, slots may be formed in the fins 68 or external surface 64 that extend substantially parallel or transverse to the center axis 50.

A heat transfer portion 88 is located adjacent the target rear surface 78. The heat transfer portion 88 includes a fluid channel or liquid channel 80 that extends through a section of the anode 32. The heat transfer portion 88 and heatsink portion 66 are formed with the anode 32 as one piece to form a single integrated structure or unistructure 90 that defines the device 14. In an embodiment, the liquid channel 80 includes channel inlet 82 and channel outlet 84 portions connected to the inlet 26 and outlet 28 conduits, respectively. A channel intermediate portion 86 is located between the channel inlet 82 and channel outlet 84 portions. In accordance with an aspect of the invention, the intermediate portion 86 is located adjacent or in relatively close proximity to the target rear surface 78 of the target 54 so as to enable the transfer of heat from the focal spot 62 to the cooling liquid 48 and provide spot cooling of the focal spot 62. It understood that other configurations may be used to route the liquid channel 80 or intermediate portion 86 in relatively close proximity to the focal spot 62 to provide spot cooling of the focal spot 62. The pump 20 is configured to continuously move the cooling liquid 48 through the inlet conduit 26, the channel inlet 82, intermediate 86 and outlet 84 portions, and the outlet conduit 28 thus removing heat from the focal spot 62 (i.e. spot cooling the focal spot 62) and forming an active heat transfer arrangement. In accordance with an aspect of the invention, the cooling liquid 48 moves at a flow rate sufficient to continuously remove sufficient heat from the focal spot 62 such that the X-ray generator 12 is not damaged or otherwise compromised.

In an embodiment, the flow rate of the cooling liquid 48 may be increased or decreased as desired by adjusting an operating parameter of the pump 20 in order to increase or decrease, respectively, the amount of heat removed from the focal spot 62. The cooling liquid 48 may be any type of liquid that provides suitable heat transfer for cooling the focal spot 62. In an embodiment, ethylene glycol, water or a combination thereof may be used as the cooling liquid 48. During use, the cooling liquid 48 expands as it absorbs heat from focal spot 62. In addition, the cooling liquid 48 may be exposed to elevated temperatures during shipping of the X-ray generator 12. The expansion reservoir 30 serves to accommodate expansion of the cooling liquid 48 due to heat absorption.

In accordance with an aspect of the invention, the anode 32 is cooled by transferring heat from the anode 32 to surrounding air via the fins 76 whereas the focal spot 62 is spot cooled by the cooling liquid 48 that is moved in the liquid channel 80 and conduits 26, 28, 46 by the pump 20. This arrangement reduces the complexity and size of the cooling system 10 and expansion reservoir 30 as compared to an X-ray generator that utilizes a separate cooling system having an external heat exchanger for cooling both the anode 32 and the focal spot 62. In particular, it has been determined by the inventors herein that for a given pump, the flow of cooling liquid 48 is substantially increased (for example, the flow of cooling liquid is increased by more than approximately 20%) by only flowing through the X-ray generator 12 as compared to also having to move the cooling liquid 48 through an external heat exchanger. This results in improved cooling and thus higher performance of the cooling system 10 and/or being able to use a smaller or less costly pump. Further, the process used for filling the expansion reservoir 30 is simplified and the likelihood of exposure to the cooling liquid 48 by patients, or contamination of the X-ray generator 12, due to leakage of the cooling liquid 48 is reduced since the volume of cooling liquid 48 is reduced. In an alternate embodiment, the heatsink portion 66 may include an opening that receives the anode 32.

In an embodiment, the pump 20 circulates the cooling liquid 48 only when the X-ray generator 12 is turned on (i.e. during CT scanning, for example) to remove heat from the focal spot 62. When the X ray generator 12 is turned off, cooling may be achieved via the fins 76. Alternatively, the pump 20 may be left on after the X-ray generator 12 is turned off. When this occurs, the anode 32 is cooled via the fins 76 and the cooled anode 32, in turn, cools the cooling liquid 48 flowing through the device 14.

In an aspect, the invention enables operation of the X-ray generator 12 at higher power for a longer duration while using a smaller focal spot. The invention also reduces the amount of time needed between scans to cool the X-ray generator 12. Further, the invention enables a reduction in volume of the cooling system 10 which lowers cost. This also enables a substantial reduction in size of the X-ray generator 12 and a corresponding reduction in size of an overall system that includes the X-ray generator 12. For example, a size of an X-ray tube may be reduced to provide a compact portable CT imaging system for imaging the head of a patient that fits into a relatively small footprint. The small size of the portable CT imaging system facilitates location of the portable CT imaging system in a patient's room and behind the head end of the patient's bed. Further, the invention provides a portable CT imaging system that operates at relatively high power while using a sufficiently small focal spot that provides high spatial resolution images when imaging cerebral blood vessels. The invention may also be used in other applications that require continuous operation of an X-ray tube at a higher steady state power such as industrial X-ray systems, including airport security systems.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A heat transfer device used in an X-ray generator having a cathode and an anode that includes a target having a focal spot, wherein heat is generated in the anode and the focal spot during an operation of the X-ray generator, comprising:
    a heatsink portion formed with the anode, the heatsink portion having a plurality of fin elements that transfer heat from the anode to surrounding air to cool the anode; and
    a heat transfer portion formed with the anode, wherein the heat transfer portion includes a liquid channel having a cooling liquid, wherein the liquid channel is located adjacent to the target to enable a transfer of heat from the focal spot to the cooling liquid to cool the focal spot, and wherein the heatsink portion, the heat transfer portion, and the anode form a unistructure.

2. The heat transfer device according to claim 1, wherein the liquid channel includes a channel inlet portion, a channel outlet portion, and a channel intermediate portion located between the channel inlet portion and the channel outlet portion, and the channel intermediate portion provides spot cooling of the focal spot.

3. The heat transfer device according to claim 2, wherein the channel intermediate portion is located adjacent a target rear surface of the target to enable cooling of the focal spot.

4. The heat transfer device according to claim 1, further including a circulation pump that moves the cooling liquid in the liquid channel.

5. The heat transfer device according to claim 1, further including an expansion reservoir that accommodates increases in a volume of the cooling liquid due to a heat absorption.

6. The heat transfer device according to claim 1, further including a fan that flows cooling air over the plurality of fin elements to increase cooling of the anode.

7. A cooling system used in an X-ray generator having a cathode and an anode that includes a target having a focal spot, wherein heat is generated in the anode and the focal spot during an operation of the X-ray generator, comprising:
    a heat transfer element attached to the anode, the heat transfer element having a plurality of fin elements that transfer heat from the anode to surrounding air to cool the anode;
    a liquid channel formed in the anode, wherein the liquid channel includes a cooling liquid, and the liquid channel is adjacent to the target, wherein heat from the focal spot is transferred to the cooling liquid to cool the focal spot, wherein the heat transfer element, the liquid channel, and the anode are unistructurally formed; and
    a circulation pump that moves the cooling liquid in the liquid channel.

8. The cooling system according to claim 7, wherein the liquid channel includes a channel inlet portion, a channel outlet portion, and a channel intermediate portion located between the channel inlet portion and the channel outlet portion, and the channel intermediate portion provides spot cooling of the focal spot.

9. The cooling system according to claim 8, wherein the channel intermediate portion is located adjacent to a target rear surface of the target to enable cooling of the focal spot.

10. The cooling system according to claim 7, further including an expansion reservoir that accommodates increases in a volume of the cooling liquid due to a heat absorption.

11. The cooling system according to claim 7, further including a fan that flows cooling air over the plurality of fin elements to increase cooling of the anode.

12. A method of cooling a focal spot and an anode in an X-ray generator, wherein the anode includes a target having a focal spot, wherein heat is generated in the anode and focal spot during an operation of the X-ray generator, comprising:
    cooling the anode by providing a plurality of fin elements on the anode that transfer heat from the anode to surrounding air to cool the anode; and
    providing a liquid channel in the anode, wherein the liquid channel includes a cooling liquid, and wherein the liquid channel is located adjacent to the target to enable a transfer of heat from the focal spot to the cooling liquid to cool the focal spot, and wherein the plurality of fin elements, the liquid channel, and the anode form a unistructure.

13. The method according to claim 12, further including providing a circulation pump that moves the cooling liquid in the liquid channel.

14. The method according to claim 13, further including circulating the cooling liquid after the X-ray generator is turned off, such that the anode is cooled via the plurality of fin elements, and the focal spot is cooled by the cooling liquid flowing through the liquid channel.

15. The method according to claim 12, further including providing a channel intermediate portion located between a channel inlet portion and a channel outlet portion, wherein the channel intermediate portion provides spot cooling of the focal spot.

16. The method according to claim 15, further including locating the channel intermediate portion adjacent to a target rear surface of the target to enable cooling of the focal spot.

17. The method according to claim 12, further including providing an expansion reservoir that accommodates increases in a volume of the cooling liquid due to a heat absorption.

18. The method according to claim 12, further including providing a fan that flows cooling air over the plurality of fin elements to increase cooling of the anode.

\* \* \* \* \*